United States Patent [19]

Yamazaki et al.

[11] Patent Number: 4,898,817

[45] Date of Patent: Feb. 6, 1990

[54] MICROORGANISM IMMOBILIZATION

[76] Inventors: Hiroshi Yamazaki, 22 Alderbrook Drive, Nepean, Ontario K2H 5W5; Sushama Joshi, 37 Sheldrake Drive, Kanata Ontario K2L 1S5, both of Canada

[21] Appl. No.: 874,388

[22] Filed: Jun. 16, 1986

[30] Foreign Application Priority Data

Nov. 6, 1985 [CA] Canada ................................ 494718

[51] Int. Cl.$^4$ ...................... C12P 35/06; C12P 17/18; C12P 7/14; C12N 11/02
[52] U.S. Cl. .................................. 435/49; 435/119; 435/161; 435/162; 435/177; 435/179; 435/180
[58] Field of Search ................. 435/49, 119, 161, 162, 435/174, 177, 179, 288

[56] References Cited

U.S. PATENT DOCUMENTS

| | | | |
|---|---|---|---|
| 3,402,103 | 9/1968 | Amberg | 435/164 |
| 4,013,514 | 3/1977 | Wildi et al. | 435/179 X |
| 4,127,447 | 11/1978 | Griffith et al. | 195/116 |
| 4,138,292 | 2/1979 | Chibata et al. | 435/179 X |
| 4,393,136 | 7/1983 | Cheetham | 435/161 |
| 4,427,775 | 1/1984 | Chen et al. | 435/174 X |
| 4,506,012 | 3/1985 | Reed | 435/139 |
| 4,546,081 | 10/1985 | Yemada et al. | 435/161 |
| 4,655,924 | 4/1987 | Heijnen | 435/174 X |

OTHER PUBLICATIONS

Atkinson, et al., Trans. Instn. Chem. Engrs., vol. 50, 1972, pp. 208-216.
Atkinson, et al., Biotechnology & Bioengineering, vol. XVII, 1975, pp. 1245-1267.
Abbott, B. J., Immobilized Cells, Annual Reports on Fermentation Processes, vol. 2, Academic Press, 1928, pp. 205-208.
Olson et al., Immobilized Enzymes in Food and Microbial Processes, Plenum Press, N.Y., 1974, pp. 176-177.

*Primary Examiner*—David M. Naff
*Attorney, Agent, or Firm*—Steele, Gould & Fried

[57] ABSTRACT

An improved repetitive, batch-type fermentation process is provided. It includes a first, non-repetitive step of forming a support bearing a film of live and reproductive microorganisms immobilized thereon, e.g. using a cloth support. Then, the process involves the steps of freely suspending and stirring small segments of support cloth bearing a fixed film of live and reproductive microorganisms immobilized thereon within a fermenter containing suitable nutrient liquor to carry out a fermentation process, whereby the microorganisms produce a fermented liquor; withdrawing fermented liquor from the fermenter while retaining the support cloth within the fermenter; adding fresh nutrient to the fermenter containing the support cloth bearing the fixed film of live and reproductive microorganisms immobilized thereon; and repeating the above steps a plurality of times. This provides an improved batch-type fermentation process which minimizes the problems of start-up and which can be readily scaled-up and automated.

13 Claims, No Drawings

MICROORGANISM IMMOBILIZATION

BACKGROUND OF THE INVENTION (1.) Field of the Invention

This invention relates to an improved batch-type fermentation process.

(2.) Description of the Prior Art

Commercial fermentations are commonly carried out by batch fermentation. To start a main batch fermentation, a seed culture is prepared in 2 to 3 stages of volume scale-up. To repeat a batch fermentation, a part of the fermented culture, if rich in viable cells, may be used as an inoculum for the next fermentation though it will reduce product yield. However, this sequence is not always preferred because the fermented culture often contains substances which inhibit the growth of microorganisms. Although harvested cells can be used instead, harvest and readdition of cells add to the cost of fermentation and these steps are less amenable to automation.

For example, in the brewing of beer, bittered wort is pitched with yeast of various moisture contents and is transferred to a vessel for batch fermentation. For true ales and stouts, *Saccharomyces cerevisiae* is used to ferment the wort for four to six days at about 15°–20° C., the yeast rising to the surface and being skimmed off later. The yeast may be reused as described above. For lager, *Saccharomyces carlsbergensis* is used to ferment the wort for from about ten to about twelve days at about 6°–8° C., the yeast and the lager being run-off into conditioning vessels.

As another example, in the production of penicillin, a large volume of concentrated, actively growing fungal suspension of *Penicillium chrysogenum* mold is required for the main fermenting tanks, to keep the fermentation time to a minimum. This is obtained in three stages. First, the selected culture is transferred from cold storage to a culture medium to produce an initial inoculum. This inoculum is then cultured in shake flasks to give a suspension. Finally, the suspension is grown in seed tanks in the plant for about 24–28 hours to the desired volume and concentration before transfer to the main fermenters. Fermentation is continued for three to five days, during which the vessel is cooled to keep the temperature between about 23°–27° C. and stirred and aerated with sterilized air. The introduction of large volumes of air causes frothing, which is controlled by the addition of antifoams. When fermentation is complete, the mycelium is removed on a rotary filter and the penicillin extracted into an organic solvent (such as butyl acetate or methyl isobutyl ketone), after acidification.

Fermentation of ethanol from carbohydrates is also now receiving attention as a future fuel and chemical feedstock. The use of ethanol as a gasoline additive is also increasing. A blend of gasoline with about 10% ethanol has been shown to increase the octane rating and to reduce emissions of nitrogen oxides and carbon monoxide. In North America, most industrial ethanol is currently made from ethylene derived from petroleum sources. However, as the price of ethylene is sharply increasing, production of fermentation ethanol will continue to rise. More efficient and economic technology of ethanol fermentation is thus desired. The industrial production of ethanol by fermentation thus demands efficiency of fermentation and low cost of substrates. Immobilization of ethanol-producing microorganisms would not only permit reuse of cells but would also accelerate ethanol production. Cells entrapped in polysaccharide gels have been most extensively studied.

Attempts have been made to avoid the problems and delays of start-up in batch type fermentations by the use of continuous fermentation. For example, some beer is brewed continuously in New Zealand. Also, some patents describe the use of continuous fermentations. For example, Amberg et al, U.S. Pat. No. 3,402,103 patented Sept. 17, 1968 taught a process in which spaced packing surfaces were disposed vertically in a tower, and fermenting organisms were grown on the packing surfaces. Thin films of carbohydrate-containing liquor were flowed substantially vertically downwardly without substantial change of direction over the organism surface so that the residence time of the feed liquor in the tower was less than about 30 minutes. Substantial conversion of carbohydrate to fermentation product, e.g. of the order of about 90%, was said to be achieved in one pass without recycling the liquor.

Griffith et al, in U.S. Pat. No. 4,127,447 patented Nov. 28, 1978 taught a continuous, biologically-catalyzed reaction with anaerobic microorganisms attached to a support in an upflow packed bed column. In the patented process, growth of the microorganisms was restricted to prevent the microorganisms from plugging the column by limiting the availability of an essential nutrient and/or by the presence of predatory protozoa which consume the anaerobic microorganisms. A membrane disruptive detergent was optionally provided in the column to lyse dead microorganisms to make them available as nutrients for live microorganisms.

Cheetham, in U.S. Pat. No. 4,393,136 patented Jul. 12, 1983 provided a continuous process for converting glucose, or other substrate to ethanol using immobilized bacterial cells under conditions which prevented growth of cells, e.g., by presenting the carbohydrate to the bacterial cells in a medium which is nutritionally inadequate for growth of such cells by lacking at least one factor required therefor.

Finally, Reed, in U.S. Pat. No. 4,506,012 patented Mar. 19, 1985 provided an improved process for preparing organic acids by a continuous homoacidogenic fermentation. This process provided increased volumetric productivity of the acid by employing a microorganism growing on the surface of a support material, e.g. activated carbon or corn cob granules.

However, continuous fermentations are not satisfactory solutions to avoid the problems of start-up of fermentations because continuous fermentations do not effeciently use the nutrients in the medium. Moreover, there is no effective simple way to reduce contamination in such continuous fermentation processes.

Previously, the present inventors have immobilized *Saccharomyces cerevisiae* cells onto epichlorohydrin triethanolamine (ECTEOLA)-cotton cloth to develop an ethanol-producing yeast film. In that method, a coiled yeast film placed in a cylindrical fermentor efficiently produced ethanol from sugars in the hydrolysate of Jerusalem antichoke tubers. Jerusalem artichoke represents a realistic source of ethanol in northern climates where it grows well and yields the highest amounts of carbohydrates (largely inulin) in its tubers. However, the preparation of ECTEOLA-cloth involves the use of unsafe chemicals and the cylindrical fermentor employed was not amenable to scale-up.

SUMMARY OF THE INVENTION

Aims of the Invention

Accordingly an object of this invention is to provide an improved batch-type fermentation process which minimizes the problems of start-up and which can be readily scaled-up and automated.

STATEMENT OF INVENTION

By this invention, there is provided a repetitive batch fermentation process comprising the steps of: (a) freely suspending and stirring small segments of support cloth bearing a fixed film of live and reproductive microorganisms immobilized thereon within a fermenter containing suitable nutrient liquor to carry out a fermentation process, whereby the microorganisms produce a fermented liquor; (b) withdrawing fermented liquor from the fermenter while retaining the support cloth within said fermenter; (c) adding fresh nutrient to the fermenter containing the support cloth bearing said fixed film of live and reproductive microorganisms immobilized thereon; and (d) repeating steps (a), (b) and (c) a plurality of times.

OTHER FEATURES OF THE INVENTION

The live and reproductive microorganisms may be a microorganism, i.e. *Bacillus subtilis, Brevibacterium ammoniagenes, Corynebacterium glutamicum, Escherichia coli, Escherichia coli* harbouring plasmids, e.g. pBR322 and K99, *Bacillus megaterium, Rhizobium meliloti*, a variety of *Streptomyces* species, e.g. *S olivochromogenes, S. clavuligerus* (NRRL 3585), [thereby to produce Cephalosporin C.] and *S. cattleya* (ATCC 29203), [thereby to produce thienamycin] or it may be a yeast, e.g., *Saccharomyces cerevisiae, Saccharomyces carlsbergensis, Kluyveromyces marxianus*, and *Kluyveromyces fragilis*.

The immobilization support may be a polyester cloth, a cellulose acetate cloth, a cellulose triacetate cloth, a cotton flannel cloth, a polyethylenimine-coated cotton cloth, or a cellulose sponge.

The microorganism forms a film of immobilized live and reproductive cell population on the cloth (designated "cell cloth") when the microogranism is allowed to grow on the cloth moistened with the nutrient liquor.

The fermentation process may be carried out by freely suspending and stirring small segments of the cell cloth in the nutrient or substrate solution. This process permits ready separation of the immobilized cells from fermentation or reaction products, and the continuous use thereof. Furthermore, the cloth provides a large surface area for the transport of both substrate and products. Agitation of free suspension provides an advantage that all the catalyst molecules substantially equally participate in catalysis.

For aerobic fermentations, sufficient air is provided in small batches by shaking; for larger batches, sufficient air is provided by forced upward aeration.

GENERALIZED DESCRIPTION OF THE INVENTION

The present invention relates in general to the immobilization of living microbial cells onto cloth, e.g. cotton cloth and to the use of the resulting cloths bearing a film of live and reproductive microorganisms immobilized thereon for repeated batch fermentation.

The microorganism is immobilized on the surface of a film material in a manner known to those skilled in the art and the immobilized cells efficiently reproduce free cells, so that segments of the microbial film can be permanently placed in a stirred tank as a resident inoculum. At the end of fermentation, the fermented culture can be separated from the microbial film. It is now known that yeasts can be colonized onto cotton cloth and that the resulting yeast films can efficiently covert hexose sugars to ethanol. Now, by the present invention, several bacteria may be immobilized on cotton cloth and may be used in batch fermentations.

In particular it is now known that many *Streptomyces* species are major producers of antibiotics. The antibiotic Thienamycin, a new β-lactam antibiotic which has advantages over other β-lactem antibiotics, namely that it has a broad antibacterial spectrum and a high resistance to β-lactamase, is provided by *S. cattleya*. It is also known that Cephalosporin C, a starting molecule for many semi-synthetic Cephalosporin derivatives is produced by *S. Clavuligerus*. By this invention, *S. Cattleya* and *S. Clavuligerus* may be immobilized on cloth, and then used as a resident inoculum in batch fermentations for the production of their respective antibiotics.

DETAILED DESCRIPTION OF THE INVENTION

Examples of the Invention

The following are examples of this invention.

EXAMPLE 1

The cloths upon which the microorganisms were immobilized were cloths of polyester, acetate, triacetate and cotton (flannel) and polyethylenimine coated cotton cloth (known as PEI-coated cotton cloth). The PEI-coated cotton cloth was prepared as described in copending U.S. Pat. application Ser. No. 691,485 filed Jan. 14, 1985, now abandoned.

The characteristics of some of the bacteria used are listed below in Table 1. *E. coli* Crooks and B41 were grown in 0.5% glucose in M63 medium and other bacteria were grown in glucose M63 supplemented with 0.1% yeast extract. The cultures were shaken at 240 rpm and 37° C. for *E. coli* strains or 30° C. for other bacteria. Cell mass density was measured by absorbance of 500 nm ($A_{500}$). One absorbance unit (absorbance 1) of *E. coli* cultures contains approx. $5 \times 10^{11}$ cells.

TABLE 1

Characteristics of bacteria immobilized on cloths.

| Bacterium | Products | Doubling times[a] | $A_{500}$ (stationary)[b] |
|---|---|---|---|
| *Bacillus subtilis* (ATCC 6051) | Amylases and proteases | 1.1 | 3.0 |
| *Brevibacterium ammoniagenes* (ATCC 6872) | Nucleotides | 1.25 | 8.8 |
| *Corynebacterium glutamicum* (ATCC 21526) | L-lysine | 1.15 | 7.5 |
| *Escherichia coli* (Crooks (ATCC 8739)[c] | Inducible enzymes | 1.0 | 6.0 |
| *Escherichia coli* HB101[d] | Recombinant DNA | 0.8 | 8.5 |

TABLE 1-continued

| | Characteristics of bacteria immobilized on cloths. | | |
|---|---|---|---|
| Bacterium | Products | Doubling times[a] | $A_{500}$ (stationary)[b] |
| *Escherichia coli* 841[e] | K99 pili | 1.2 | 5.5 |

[a]Doubling times of free cells in h.
[b]Absorbance at 500 pm of stationary cultures.
[c]Because of its high cyclic AMP content (Fraser and Yamazaki, 1978). It can be used for production of inducible catabolic enzymes whose synthesis depends on cyclic AMP (e.g. L-aspartase and penicillin acylase).
[d]Because it lacks modification, restriction and recombination systems (Maniatis et al., 1982). It is commonly used for hosting recombinant DNA.
[e]It harbors K99 plasmid and thus produces K99 pili which can be used as a vaccine against *E. coli* scours in domestic animals.

In addition to the above bacteria, the following bacteria have also been immobilized in cotton cloth:
*Bacillus amyloliquefaciens* (for amylase producer);
*Bacillus megaterium* (for various metabolites);
*Rhizobium meliloti* (for azofication inoculant);
*Streptomyces olivochromogenes* (for glucose isomerase);
and other *Streptomyces* species (for various antibiotics).

The bacterial immobilization was initiated as follows. Stationary cultures, e.g., whose $A_{500}$ are given in Table 1) were diluted 100 fold with fresh medium and added to a culture tube containing 1 cm square segments of cloth (e.g. cotton flannel) to cover the cloth. After 1 h, excess liquid was removed, and the bacteria attached to the cloth were allowed to grow on the wet cloth. Alternatively, the cloth could be left in the culture for about 24 h. After 24 h, the segments were rinsed once with fresh medium and incubated for about 24 h, after which this was repeated once more. The culture tube was then filled with fresh medium and shaken at 240 rpm overnight. Next day (hereinafter designated "first day") and on the following days, the specific rate of cell mass generation from the cloth segments (bacterial films) was measured as follows: One bacterial film was vigorously washed 5 times by vortexing in 3 ml of medium followed by decantation. Each film was first activated by incubation in 1 ml of fresh medium for 2 to 3 h, washed as before, and shaken in 1 ml of fresh medium at 240 rpm. After about 60 min, $A_{500}$ was determined and the specific rate of cell mass generation from the film was calculated as described hereinafter. Every 24 h, culture liquid was replaced with fresh medium and the specific rate of cell mass generation was measured at least once a week for 60 days.

Cotton flannel (cotton cloth) was briefly immersed in a dilute bacterial suspension in fresh medium. The bacteria attached to the cloth were allowed to grow on the wet cloth, and the cloth was rinsed daily with fresh medium over 3 days. The cloth was then shaken in growth medium. Next day, the cloth (bearing a bacterial film) was thoroughly washed by vigorous vortexing (to remove any loosely attached bacterial cells) and then assayed for its capacity to generate cell mass. On the first day, the specific rates of cell mass generation from the bacterial films varied with bacteria. The rates increased with days of liquid culturing to plateau levels which varied with bacteria ranging between about $3 \times 10^{-4}$ and about $4 \times 10^{-4}$ absorbance units/h/cm². The times required to reach the plateau levels varied widely from 5 days for *Brevibacterium ammoniagenes* to 11 days for *Bacillus subtilis*. To examine the longevity of the films as resident inocula, the films were washed daily by vigorously vortexing the films in fresh medium. The plateau rates of cell mass generation from the films did not change for at least 60 days.

Other cloth materials were similarly examined for their capacity to form bacterial films. The results of these examinations are shown in Table 2 below:

TABLE 2

| | Specific rates of cell mass generation from bacteria immobilised on various cloths | | | | |
|---|---|---|---|---|---|
| | Specific rate ($10^{-4}$ absorbance units/h/cm² cloth)[a] | | | | |
| Bacterium | Polyester | Acetate[b] | Triacetate[b] | PEI-cotton | Cotton |
| *Bacillus subtilis* | 0.6 | 0.4 | 0.3 | 1.2 | 3.6 |
| *Brevi. ammoniagenes* | 0.3 | 0.4 | 0.3 | 0.8 | 3.8 |
| *Coryne. glutamicum* | 3.0 | 0.1 | 0.2 | 0.7 | 3.7 |
| *E. coli* Crooks | 0.0 | 0.2 | 0.0 | 2.6 | 3.5 |
| *E. coli* HB101 | 0.3 | 0.4 | 0.4 | 3.2 | 3.2 |
| *E. coli* B41 | 0.1 | 0.2 | 0.2 | 3.7 | 3.6 |

Table Legends (a) Bacteria were immobilized on various cloths as described above. After 3 days growth on wet cloths, the cloths were shaken in growth medium which was changed daily. After 16 days of liquid culturing, the specific rates were determined as described above.

(b) Cellulose acetate or triacetate cloth.

Table 2 shows that cotton cloth was superior as an immobilization support to polyester, acetate, triacetate and PEI-coated cotton cloths. Although PEI-coated cotton cloth was effective in immobilizing *E. coli* strains, it was less effective for the other bacteria.

As also shown above in Example 1, several bacteria of industrial importance were found to form immobilized populations on cotton cloth. The resulting bacterial films generated free cells at significant rates which remained constant for at least about 60 days. By retaining these films in a fermentor, the films are useful as resident inocula in repeated batch fermentations. The immobilized cells could not be released even after vigorous mixing. Since the resulting bacterial films can generate free cells at significant rates and can be easily retained in a fermentor, they can be used as resident inocula which facilitates automation of repeated batch fermentations.

The immobilized inoculum method is less susceptible to problems of contamination than procedures which depend on free cells (e.g. continuous culture) because the contaminants will be flushed from a fermentor (provided that the immobilized cells will not be replaced by the contaminants). The resident inoculum method is particularly suitable for continuous production of pathogenic bacteria as it eliminates a possible risk in preparing and transferring an inoculum culture. An *E. coli* harboring pBR322 plasmid has been immobilized on cotton cloth and the immobilized cell stably maintains the plasmid, generating free cells containing the plasmid. Since pBR322 and its derivatives are popular cloning vectors, the method described herein is useful for the continuous production of recombinant DNA molecules and their products.

An equation for the rate of cell mass generation from the resident inocula may be developed as follows:

At time 0, a bacterial film is suspended in growth medium (containing no cells). The film generates free cells at R (absorbance units/h). Free cells generated from the film double at a doubling time of D h. After time t h, absorbance of the culture is taken. Since the absorbance of the culture is proportional to cell mass density, absorbance × volume (1) of the culture (absorbance unit in 1) measures cell mass present in the culture. The rate (R) of cell mass generation is $$R = \frac{aM}{e^{at} - 1}$$

where $a = 0.693/D$; $M$ = cell mass (absorbance units in 1) in the fermentor; $t$ = fermentation time in h. If the area of the film is known, the specific rate ($R_s$) of cell mass generation (absorbance units/h/cm$^2$) can be calculated. If cell mass M is desired in the fermentor after time t, the area of the film required in the fermentor is $R/R_s$ cm$^2$.

This equation may be used to calculate the area of film required to obtain a desired cell mass in a given fermentation time. For example, if one liter of an *E. coli* Crooks (D=1h) culture having $A_{500}$ of 6 is desired after 8 h fermentation, M=6 absorbance units and $R = 1.63 \times 10^{-2}$ absorbance units/h.

Since $R_s$ of the *E. coli* Crooks film is $3.5 \times 10^{-4}$ absorbance units/h/cm$^2$ (Table 2), the fermentor should contain $R/R_s = 47$ cm$^2$ of the film. Since 1 absorbance unit of this bacterium corresponds to approx. $5 \times 10^{11}$ cells, 1 l of this culture contains approx. $3 \times 10^{12}$ cells. If fermentation is repeated 3 times a day, this 1 l-fermentor will yield approx. $10^{13}$ cells per day.

Since the films show stable and constant rates of cell mass generation, the rate and extent of fermentation can be reproducibly controlled by varying the area of films.

Although shaking was employed as a means of agitation and aeration in this example, either a 3-blade vertical stirrer or a 3-blade marine propeller can be used together with an air sparger at the bottom of the fermentor.

As noted above, *Streptomyces* species are major antibiotics producers. Thienamycin is a β-lactam antibiotic which has advantages over other β-lactam antibiotics since it has a broad antibacterial spectrum and a high resistance to β-lactamases.

It is known that Thienamycin is produced by *S. cattleya*. The following Example shows the production of Thienamycin using immobilized *S. cattleya* cells as resident inoculum.

EXAMPLE 2

Freely suspended Streptomyces cattleya film for Thienamycin production

*S. cattleya* (ATCC 39203) was grown in a Thienamycin production medium which contained per 1, 10g glycerol, 15 g cornsteep liquor, 10 g cottonseed meal, 15 g distiller's soluble, 0.01 g CoCl$_2$.6H$_2$O and 3 g CaCO$_3$. An incubation temperature of 30° C. was used throughout. The bacterial immobilization was initiated as in Example 1 which involved 3 day stationary growth on cotton cloth with daily medium supplementation. After immobilization, the segments were shaken in medium at 30° C. and 280 rpm overnight. The segments were washed, mixed with medium (2 ml per segment) and shaken for 3 days. Thienamycin concentrations increased with time and reached a maximum concentration (about 14 μg/ml) which is equivalent to a maximum level produced in a free cell culture. After 3 days, the segments were washed with medium and resuspended in fresh medium. This 3 day batch fermentation was repeated 20 times (60 days). Maximum Thienamycin concentration remained the same for at least 20 cycles.

Since a small volume (less than 10 ml) of medium was used, in this example, shaking was sufficient to aerate the culture.

If it is desired to carry out such fermentation in a larger fermentor, forced aeration is necessary. It has been found that fluidization of the support bearing the film of live and reproductive *Streptomyces* can be achieved by forced upward aeration. Fermentation in such an aerated fermentor exhibited the same productivity of thienamycin as in the shaken culture.

As also described above, it is known that *S. clavuligerus* produces Cephalosporin C, a starting material for many semi-synthetic Cephalosporin derivatives. In another Example, *Streptomyces clavuligerus* (NRRL 3585) was immobilized on cotton cloth in the same manner as described for *S. cattleya* in Example 2, and was used to produce Cephalosporin C.

EXAMPLE 3

Fixed Yeast Film for Ethanol Production

Yeasts were immobilized and colonized on unmodified cotton cloths. The yeasts used were *Saccharomyces cerevisiae* X2180-1B (Yeast Genetic Stock Center), *Kluyveromyces marxianus* ATCC 10606 and *Kluyveromyces fragilis* ATCC 36534.

The yeasts were immobilized as follows:

A cloth was immersed in a yeast suspension in fresh medium for at least 1h, removed from the liquid and then incubated in air for about 17 h. The cells grown in this manner were immobilized on cloth. That is, when the cloth (designated yeast film) was suspended in fresh medium, it did not release cells although the bound cells reproduced free cells after a few hours.

The yeasts were colonized in both a cylindrical film fermentor and a rectangular film fermentor, and the ethanol productivity of the *S. cerevisiae* film was studied in each of these film fermentors. For the cylindrical film fermentor, a rectangular cotton cloth was placed on a bronze screen of the same dimensions (7 cm × 15 cm). The double layer was coiled along the longer side and the coil was vertically fitted into a jacketed column (2.8 cm i.d.; 25 cm height). The average distance between the coil was 0.4 cm. The temperature of the jacket was maintained at about 30° C.

Yeast colonization on cloths was initiated as follows. A late log phase yeast culture was diluted to $4\times10^7$ cells/ml with fresh medium and added to the fermentor. After about 1 h, the fermentor was drained and the yeast was allowed to grow on the wet cloth in air for about 17 h. The fermentor was then filled with fresh medium and incubated for about 24 h.

The growth medium was prepared as follows:

Jerusalem antichoke tubers were washed, sliced, mixed with an equal weight of water, and autoclaved for 30 min. The juice, separated from the pulp by filtration, contained 7 to 8% inulin, a major carbohydrate in the tubers. The juice was autoclaved and used as a medium for the inulin-utilizing yeasts, *K. marxianus* and *K. fragilis*.

For *S. cerevisiae* which cannot use inulin, the juice was adjusted to pH 3.0 with concentrated $H_2SO_4$, autoclaved for 30 min to hydrolyze the inulin, and adjusted to pH 5.0 with concentrated $NH_4OH$. All yeasts were grown at 30° C.

Ethanol productivity of yeast cells colonized on cloth was daily determined as follows. The fermentor was drained, refilled with fresh medium, and incubated for about 2 to 3 h. After this activation period, the fermentor was drained and refilled with fresh medium. After about 60 min, ethanol was assayed, from which ethanol productivity (g ethanol produced per l of fermentor volume per hour) was calculated.

The assay of reducing sugars, ethanol, and cell mass was carried out as follows:

Reducing sugars were assayed by the 3,5-dinitrosalicyclic acid method using D-fructose as a standard. The reducing sugar content of growth media was determined after hydrolyzing inulin as described above.

Ethanol was assayed by gas chromatography.

Cell mass weight of yeast immobilized on cloth was determined by extraction with formic acid and drying at 110° C. for 1 day.

The productivity of the reactor is defined as the amount of a product produced per litre of total reactor volume divided by the liquid retention time. This term is most relevant to the design of a reactor process, and thus should be used for comparison of productivity.

Productivity can then be expressed as Pv/(TV) or PL/T for batch production and PF/V for continuous flow production where P=amount of a product per litre of liquid collected from the reactor after or during the retention time;
v=liquid volume in the reactor (liter);
V=total reactor volume (liter);
F=flow rate (liter hour);
T=retention time (hour);
L=liquid volume fraction in the reactor (v/V).

Some researchers use PF/V as productivity for continuous flow production. Since this term is equal to P/T or PF/(VL), it should be multiplied by L to obtain the above productivity.

The cylindrical film fermentor has been useful in examining ethanol productivity of yeast films with relatively small amounts of the substrate. However, scale-up of such a fermentor by increasing its column height will effectively reduce the liquid portion of the fermentor because evolving $CO_2$ occupies the upper part of the film. Enlarging the column diameter will decrease the efficiency of removal of heat generated by fermentation. Accordingly, for a rectangular film fermentor, a narrow width was used to facilitate dissipation of heat generated. Rectangular cloths were stretched in parallel along the length of the fermentor. Maintaining a uniform distance between the cloth layers is easier in this fermentor than in the cylindrical film fermentor. The rectangular fermentor can be scaled-up by using multiple units in parallel or by increasing its length. Furthermore circulation of the medium is feasible. Thus the rectangular film fermentor was constructed by colonizing *S. cerevisiae* on the cloth as follows:

Three rectangular cloths (5 cm$\times$30 cm) were stretched lengthwise and mounted in parallel (0.7 cm apart) in a stainless steel stand, and placed in a polymethylmethacrylate (PLEXIGLASS - registered Trade Mark) container (2.2. cm width, 32 cm length, 20 cm height, inside). Yeast colonization on cloth was performed as described for the cylindrical film fermentor. The medium was changed once a day for about 8 days until maximum ethanol productivity was attained. When ethanol productivity of the fermentor was to be determined, the fermentor was first activated by incubation in fresh medium for about 2 to 3 h, then filled with 285 ml medium (liquid volume of the fermentor) and incubated at approximately 30° C.

It has been found that ethanol productivity of the *S. cerevisiae* film increased during the first 7 days of fermentor operation. Microscopic observation and determination of cell mass showed that the yeast film thickened during this period. At the plateau, the *S. cerevisiae* film fermentor produced 16.5 g of ethanol per l per h which was similar to that obtained with ECTEOLA-cloth. Cell mass accumulated per unit area was similar (5 mg/cm$^2$). The longevity of the *S. cerevisiae film was tested for* 60 days in the cylindrical fermentor. No significant change in ethanol productivity was observed during this period.

Observation of ethanol productivity by the films of inulin-fermenting *K. marxianus* and *K. fragilis* in an unhydrolyzed extract of Jerusalem artichoke tubers produced the following results: These yeasts colonized on cloth more slowly than *S. cerevisiae* and ethanol productivity at the plateau was less than that of *S. cerevisiae*.

The rectangular film fermentor was used for ethanol production from a hydrolyzed extract of Jerusalem artichoke tubers. *Saccharomyces cerevisiae* cells were immobilized on cotton cloth. The resulting yeast films were placed in parallel in a rectangular fermentor which was designed for scale-up. Ethanol production from sugars in the hydrolysate of Jerusalem artichoke tubers was studied in the following modes of operation: (i) stationary batch; (ii) circulated batch; and (iii) continuous flow. In both batch modes, the medium was added to the fermentor and removed after ethanol fermentation was completed. The medium was not circulated in the stationary batch mode but was circulated in the circulated batch mode. In the continuous mode, the medium was continuously fed through one end of the fermentor and removed from the opposite end.

In both batch modes, it was found that the rate of ethanol production declined with time, reflecting decreasing concentrations of the substrate. Circulation of medium in the batch fermentation yielded constantly higher rates of ethanol production until the end of fermentation. Accordingly, fermentation of sugars in the circulated batch mode was completed at about 4 h as compared to about 8 h in the stationary batch mode. Maximum ethanol productivity in g ethanol per l of fermentor volume per hour was about 17 in the stationary batch mode and about 20 in the circulated batch mode, while the ECTEOLA-cloth fermentor gave about 16 in the stationary batch mode. In the continuous flow mode, similar ethanol productivity was obtained only at a high flow rate (e.g. medium retention time of about 1 h) but a large proportion of the sugars was not fermented. In this mode, complete fermentation of sugars was achieved only after a retention time of about 9.5 h. Table 3 below lists average ethanol productivity for complete sugar fermentation in the three modes. Using a timed draining and pumping device, circulated batch fermentations were automatically repeated at 4 h intervals in which all sugars (10%) were utilized and ethanol was produced at about 90% of theoretical yield.

TABLE 3

Ethanol production in a rectangular film fermentor.

| Ethanol production | Mode of operation | | |
|---|---|---|---|
| | Stationary batch | Circulated batch | Continuous flow |
| Completion time[a] | 8 | 4 | 9.5 |
| Average productivity[b] | 5.5 | 11 | 4.8 |

[a]Time (h) for conversion of all fermentable sugars to ethanol with 90% of the theoretical yield.
[b]Ethanol (g) produced per liter of fermentor volume divided by completion time.

As seen above, circulated batch fermentation gave the shortest time of fermentation and accordingly the highest average ethanol productivity.

It has thus been shown that *S. cerevisiae* can bind and propagate on cotton cloth and the resulting film can be used for continuous ethanol production. The use of unmodified cotton cloth is simpler, less expensive and safer than ECTEOLA-cloth. The film system permits freer movement of substrates and products, particularly $CO_2$ than gel entrapped cell systems.

A rectangular film fermentor has also been provided which can be scaled-up. In such a fermentor, a circulated batch mode provides a faster fermentation than the continuous mode. Circulation increases the transport of sugars to immobilized yeast cells as well as facilitating the mixing of sugars and ethanol. All the cells in the circulated batch fermentation equally share in ethanol production, whereas in the continuous mode cells colonized downstream produce ethanol at greatly reduced rates because of the lower sugar and higher ethanol concentrations. Using a circulated batch fermentation, 4 h was required to utilize all sugars (10%) to produce ethanol with 90% of theoretical yield. This gives an average productivity of 11 g ethanol per l of fermentor volume per h (Table 3). It was previously reported that *S. cerevisiae* cells entrapped in polyester foam give approximately 5 g per l of fermentor per h and those entrapped in calcium alginate gel, approximately 9 g per l per h.

In the rectangular fermentor, the yeast film was mounted 0.7 cm apart. The fermentor has a narrow width in order to facilitate heat dissipation to the surroundings. However, if the circulating medium is allowed to pass through a heat exchanger, a wider fermentor (thus with larger medium capacity) can be constructed.

EXAMPLE 4

(Freely suspended yeast film for ethanol production)

*Saccharomyces cerevisiae* cells were immobilized on cotton cloth, as described in Example 3.

*Saccharomyces cerevisiae* X2180-1B (Yeast Genetic Stock Center) grown at 30° C. was used.

The media used were a hydrolysate of Jerusalem artichoke tuber, prepared as described in Example 3, containing 10% fermentable hexoses, and a starch acid hydrolysate supplemented with $K_2HPO_4$ (final concentration 0.64%), $NH_4H_2PO_4$ (0.8%) and yeast extract (0.4%). This medium had pH of about 4.5 and contained approx. 16% (w/v) of fermentable hexoses.

The yeast film was developed as follows:

A late log phase culture of *S. cerevisiae* was diluted 10 to 100 fold with fresh media and added to the fermentor described below only to cover segments (e.g. 1 to 10 cm squares) of cotton cloth (preferably flannel). A film fermentor (250 ml capacity) is equipped with a stirrer with three vertical blades whose width is 1/6 the diameter of a cylindrical chamber, (although a conventional 3-blade marine propeller stirrer can alternatively be used.) Segments of the resulting yeast film were suspended in the above fermentor containing ethanol production media. A mixing effect to provide circulation is necessary for efficient production of ethanol is obtained by suspending segments of yeast film.

Once a day, the fermentor was drained, refilled with fresh medium to cover the segments, and stirred briefly. After 8 days, the fermentor was filled with fresh medium to its full capacity and stirred at various rates. Ethanol productivity and completion time were determined as described in Example 3.

At the end of fermentation, the segments can be retained in the tank by means of metal screen attached to the drain or pipe for removal of the fermented culture. Fresh medium is then added to repeat batch fermentation. The retention of the yeast film in the fermentor permits automation of batch ethanol fermentation.

In this Example, segments of the yeast film were stirred at various speeds in the hydrolysate of Jerusalem artichoke tubers or the starch hydrolysate. Unlike bacterial film (Example 1), the yeast film consisted of an accumulated cell mass grown from the initially adsorbed yeast cells. At excess stirring (above about 400 rpm) some yeast cell mass came off from the film, resulting in reduced ethanol productivity. At low stirring rates below about 100 rpm, ethanol productivity decreased with the rates; presumably at these rates, the stirring rate determines the rate of transport of sugars and products to and from the film. In the fermentor described above, the stirring rate of 100 to 200 rpm was found to give high ethanol productivity. A total area of the yeast film also determined ethanol productivity. The suspension of 1000–2000 cm² of the film per liter of medium was found to give high ethanol productivity.

Table 4 summarizes ethanol production from the two sugar substrates.

TABLE 4

Ethanol production by yeast film suspension in a stirred tank.

| Ethanol production | Hydrolysate | |
|---|---|---|
| | J. artichoke tuber | starch |
| productivity[a] | 20 | 20 |
| completion time[b] | 4 | 6 |

[a]Maximum ethanol productivity (g ethanol/fermentor/h) was determined as described in Example 3.
[b]Time (h) For conversion of fermentable sugars to ethanol with about 90% of the theoretical yield.

Table 4 shows that ethanol productivity in a stirred tank was the same as the circulation mode in a fixed film fermentor described in Example 3. Using a timed draining and pumping device, batch fermentations were automatically repeated in the stirred tank. No significant change in ethanol productivity was observed for at least about 60 days.

Preliminary experiments show that the following yeasts can be immobilized onto cotton cloth and used as resident catalysts for ethanol production: *Saccharomyces diastaticus, Saccharomyces uvarum* and *Schwanniomyces alluvius.*

Under appropriate stirring, sugars are thus converted to ethanol at about 90% of the theoretical yield within 4 h from the hydrolysate of Jerusalem artichoke tubers (containing 10% fermentable sugars) and within 6 h from starch hydrolysate (containing about 16% fermentable sugars).

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly equitably, and "intended" to be, within the full range of equivalence of the following claims.

We claim:

1. A repetitive batch fermentation process for producing a fermentation product comprising the steps of:
   (a) freely suspending and stirring small segments of support cloth bearing a fixed film of live and reproductive microorganisms immobilized thereon within a fermenter containing suitable nutrient liquor to carry out a fermentation process, whereby said microorganisms produce a fermented liquor;
   (b) withdrawing said fermented liquor from said fermenter while retaining said small segments of support cloth bearing said fixed film of live and reproductive microorganisms immobilized thereon within said fermenter;
   (c) adding fresh nutrient to said fermenter containing said small segments of support cloth bearing said fixed film of live and reproductive microorganisms immobilized thereon; and
   (d) repeating steps (a), (b) and (c) a plurality of times to produce said fermentation product.

2. The fermentation process of claim 1 including the preliminary step of initially forming said small segments of support cloth bearing said film of said live and reproductive microorganisms prior to step (a).

3. The fermentation process of claim 2 wherein said preliminary step of initially forming said small segments of support cloth bearing said film of microorganisms comprises: growing a stationary culture of said microorganisms in a culture vessel containing water and said small segments of cloth; removing excess water from said small segments of cloth; thereby providing small segments of water-wet cloth and allowing said microorganisms, which are attached to said small segments of water-wet cloth, to grow on said small segments of water-wet cloth.

4. The fermentation process of claim 2 wherein said preliminary step of initially forming said small segments of support cloth bearing said film of microorganisms comprises: immersing small segments of cloth in a yeast suspension in a fresh aqueous medium; and then suspending said small segments of cloth in air, thereby to provide small segments of cloth bearing a fixed film of live and reproductive yeast immobilized thereon.

5. The fermentation process of claim 1 wherein said live and reproductive microorganism is a microorganism selected from the group consisting of
   *Bacillus subtilis*
   *Brevibacterium ammoniagenes*
   *Corynebacterium glutamicum*
   *Escherichia coli*
   *Bacillus amyloliquefaciens*
   *Bacillus megaterium*
   *Rhizobium meliloti*
   *Streptomyces olivochromogenes*
   *Streptomyces clavuligerus*
   and *Streptomyces cattleya.*

6. The fermentation process of claim 5 wherein said live and reproductive microorganism is *Streptomyces cattleya*, and wherein said fermentation product is thienamycin.

7. The fermentation process of claim 5 wherein said live and reproductive microorganism is *Streptomyces clavuligerus* and wherein the fermentation product is Cephalosporin C.

8. The fermentation process of claim 1 wherein said live and reproductive microorganism is *Kluyveromyces marxianus*, and the fermentation product is ethanol.

9. The fermentation process of claim 1 wherein said live and reproductive microorganism is *Kluyveromyces fragilis*, and wherein the fermentation product is ethanol.

10. The fermentation process of claim 1 wherein said support cloth is a polyester cloth, a cellulose acetate cloth, a cellulose triacetate cloth, a cotton flannel cloth, or a polyethylenimine-coated cloth.

11. The fermentation process of claim 1 carried out as a circulating batch fermentation.

12. The fermentation process of claim 1 carried out aerobically by shaking.

13. The fermentation process of claim 1 carried out aerobically by forced upward aeration.

* * * * *